US006310007B1

(12) United States Patent
Kuo et al.

(10) Patent No.: US 6,310,007 B1
(45) Date of Patent: Oct. 30, 2001

(54) 7,10,12-TRIHYDROXY-8(E)-OCTADECENOIC ACID AND DERIVATIVES AND USES THEREOF

(75) Inventors: Tsung Min Kuo; Ching T. Hou, both of Peoria, IL (US)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 09/523,330

(22) Filed: Mar. 10, 2000

Related U.S. Application Data

(60) Provisional application No. 60/125,489, filed on Mar. 22, 1999.

(51) Int. Cl.[7] ..................... A01N 37/00

(52) U.S. Cl. ..................... 504/313; 504/320; 504/321; 504/325; 554/103; 554/104; 554/213; 554/219; 554/223; 554/224; 554/225; 554/229

(58) Field of Search ..................... 554/213, 219, 554/229, 225, 223, 224, 103, 104; 504/313, 320, 321, 325

(56) References Cited

U.S. PATENT DOCUMENTS

| | | | |
|---|---|---|---|
| 4,151,817 | 5/1979 | Mueller | 123/90.16 |
| 4,205,634 | 6/1980 | Tourtelot, Jr. | 123/90.15 |
| 4,498,352 | 2/1985 | Hedelin | 74/568 R |
| 4,522,085 | 6/1985 | Kane | 74/568 R |
| 4,770,060 | 9/1988 | Elrod et al. | 74/665 L |
| 4,771,742 | 9/1988 | Nelson et al. | 123/90.17 |
| 4,887,563 | 12/1989 | Ishida et al. | 123/90.16 |
| 4,917,058 | 4/1990 | Nelson et al. | 123/90.17 |
| 5,136,887 | 8/1992 | Elrod et al. | 74/569 |
| 5,161,429 | 11/1992 | Elrod et al. | 74/569 |
| 5,553,573 | 9/1996 | Hara et al. | 123/90.15 |
| 5,622,144 | 4/1997 | Nakamura et al. | 123/90.15 |
| 5,852,196 | 12/1998 | Hou | 554/103 |

OTHER PUBLICATIONS

Kuo et al, JAOCS, vol. 75(7), pp. 875–879, May 1998.*

(List continued on next page.)

*Primary Examiner*—Deborah D. Carr
(74) *Attorney, Agent, or Firm*—M. Howard Silverstein; Curtis P. Ribando; John D. Fado

(57) ABSTRACT

The compound 7,10,12-trihydroxy-8(E)-octadecenoic acid (TOD) has been produced by bioconversion of ricinoleic acid by *Pseudomonas aeruginosa* PR3. TOD and derivatives thereof are useful for controlling biological organisms, such as fungi and insects.

19 Claims, 1 Drawing Sheet

OTHER PUBLICATIONS

Figure 1:
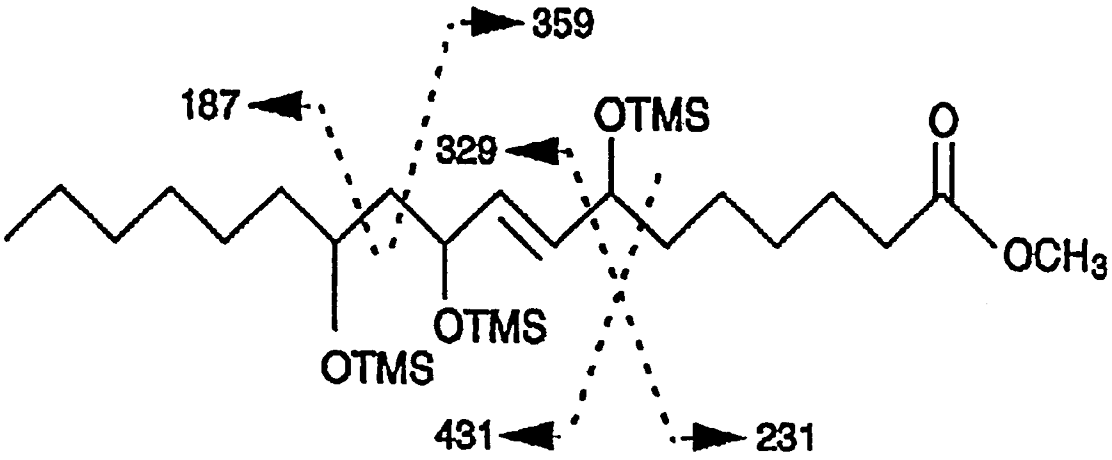

A Naturally Aspirated Miller Cycle Gasoline Engine—Its Capability of Emission, Power and Fuel Economy, SAE Technical Paper Series, No. 960589, Feb. 26–29, 1996.

An Initial Study of Variable Valve Timing Implemented with a Secondary Valve in the Intake Runne, SAE Technical Paper Series, No. 960590, Feb. 26–29, 1996.

Controlling Engine Load by Means of Late Intake–Valve Closing, SAE Technical Paper Series, No. 800794, Jun. 9–13, 1980.

Effects of Intake–Valve Closing Timing on Spark–Ignition Engine Combustion, SAE Technical Paper Series, No. 850074, Feb. 25–Mar. 1, 1985.

T.M. Kuo et al, "Fatty Acid Bioconversions by *Pseudomonas aeruginosa* PR3" *American Oil Chemists Society 89$^{th}$ Annual Meeting Abstracts*, May 10–13, Chicago, IL, p. 73 (1998).

T.M. Kuo et al., "Fatty Acid Bioconversions by *Pseudomonas aeruginosa* PR3" *JAOCS*, vol. 75, No. 7, pp. 875–879 (1998).

C.T. Hou et al., "Production of a New Compound, 7,10–Dihydroxy–8(E)–Octadecenoic Acid from Oleic Acid by Pseudomonas sp. PR3", *J. Indust. Microbiol. 7*:123–130, (1991).

C.T. Hou et al., "A Novel Compound, 12,13, 17–Trihydroxy–9(Z)–Octadecenoic Acid, from Linoleic Acid by a New Microbial Isolate Clavibacter sp. ALA2", *J. Am. Oil Chem. Soc. 73*:1359–1362, (1996).

H. Suemune et al., "Synthesis of Unsaturated Trihydroxy C–18 Fatty Acids Isolated from Rice Plants Suffering from Rice Blast Disease", *Chem. Pharm. Bull. 36*:3632–3637, (1988).

B. Gosse–Kobo et al., "Total Synthesis of Unsaturated Trihydroxy C–18 Fatty Acids", *Tetrahedron Lett. 30*:4235–4236, (1989).

T. Kato et al., "Structure and Synthesis of 11,12, 13–Trihydroxy–9(Z), 15(Z)–Octadecadienoic Acids from Rice Plant Suffering Rice Blast Disease", *Chem Lett. 27*:577–580, (1986).

H. Masui et al., "An Antifungal Compound, 9,12, 13–Trihydroxy–(E)–10–Octadecenoic Acid from *Colocasia antiquorum* Inoculated with *Ceratocystis fimbriata", Phytochemistry 28*:2613–2615, (1989).

* cited by examiner

7,10,12-TRIHYDROXY-8(E)-OCTADECENOIC ACID AND DERIVATIVES AND USES THEREOF

This application claims benefit of Prov. No. 60/125,489 filed Mar. 22, 1999.

BACKGROUND OF THE INVENTION

1. Field of the Invention

This invention relates to a novel trihydroxy unsaturated fatty acid, 7,10,12-trihydroxy-8(E)-octadecenoic acid (TOD), which is produced from ricinoleic acid by *Pseudomonas aeruginosa* strain PR3.

2. Description of the Prior Art

Microbial conversions of unsaturated fatty acids have been widely exploited to produce new, value-added products. Hou, (C. T Hou, "Microbial Oxidation of Unsaturated Fatty Acids", *Advances in Applied Microbiology* Vol. 41, pp. 1–23, 1995) recently reviewed the work on some biological oxidation systems. Wallen et al., (L. L. Wallen et al., "The Microbiological Production of 10-Hydroxystearic Acid from Oleic acid", *Arch. Biochem. Biophys.* 99:249–253, 1962) reported the first bioconversion of oleic acid to 10-hydroxystearic acid by a Pseudomonad. The bioconversion of fatty acids to produce mono-, di-, and tri-hydroxy unsaturated fatty acids has also been found (A. C. Lanser et al., "Production of 15-, 16- and 17-Hydroxy-9-Octadecenoic Acid from Oleic Acid with *Bacillus pumilus", J. Am. Oil Chem. Soc.* 69:363–366, 1992), (C. T. Hou et al., "A Novel Compound, 7,10-Dihydroxy-8(E)-Octadecenoic Acid from Oleic Acid by Bioconversion", *J. Am. Oil Chem. Soc.* 68:99–101, 1991), (C. T. Hou et al., "Production of a New Compound, 7,10-Dihydroxy-8(E)-Octadecenoic Acid from Oleic Acid by Pseudomonas sp. PR3", *J. Indust. Microbial.* 7:123–130, 1991) and (C. T. Hou et al., "A Novel Compound, 12,13,17-Trihydroxy-9(Z)-Octadecenoic Acid, from Linoleic Acid by a New Microbial Isolate Clavibacter sp. ALA2", *J. Am. Oil Chem. Soc.* 73:1359–1362, 1996). The production of a novel compound, 7,10-dihydroxy-8(E)-octadecenoic acid (DOD) from oleic acid by strain PR3 has been described most extensively. Under optimal conditions, the yield of bioconversion is greater than 60%, (C. T. Hou et al., "Production of a New Compound, 7,10-Dihydroxy-8(E)-Octadecenoic Acid from Oleic Acid by Pseudomonas sp. PR3", *J. Indust. Microbiol.* 7:123–130, 1991). PR3 is a strain of *Pseudomonas aeruginosa*, and its DOD production is inversely correlated with the accumulation of phenazine 1-carboxylic acid (PCA), (C. T. Hou et al., "Identification of NRRL Strain B-18602 (PR3) as *Pseudomonas Aeruginosa* and Effect of Phenazine-1-Carboxylic Acid Formation on 7,10-Dihydroxy-8(E)-Octadecenoic Acid Accumulation", *World J. Microbiol. Biotechnol.* 9:570–573, 1993). The production of DOD and PCA by strain PR3, however, was not consistent, and studies were conducted to stabilize and maximize cultures for the bioconversion of oleic acid.

Oxygenated metabolites of unsaturated fatty acids play a variety of important roles in biological systems. Enzymatic conversion of lipid hydroperoxides to trihydroxy fatty acids has been reported in many higher plants, (B. A. Vick et al., "Oxidative Systems for Modification of Fatty Acids: The Lipoxygenase Pathway", *The Biochemistry of Plants: A Comprehensive Treatise* Vol. 9, pp.53–90, 1987). 8,9,13-Trihydroxy docosanoic acid is an extracellular lipid component in yeast, (F. H. Stodola et al., "8,9,13-Trihydroxydocosanoic Acid, an Extracellular Lipid Produced by a Yeast", *Biochemistry* 4:1390–1394, 1965).

9,10,13-Trihydroxy-11(E)- and 9,12,13-trihydroxy-10(E)-octadecenoic acids were detected in beer, (A. Graveland, "Enzymatic Oxidations of Linoleic Acid and Glycerol-1-Monolinoleate in Doughs and Flour-Water Suspensions", *J. Am. Oil Chem. Soc.* 47:352–361, 1970) and presumably resulted from converting linoleic acid during the barley malting process, (C. Baur et al., "Investigation about the Taste of Di-,Tri- and Tetrahydroxy Fatty Acids", *Z. Lebensm. Unters. Forsch.* 165:82–84, 1977). Trihydroxy unsaturated fatty acids, 9S,12S,13S-trihydroxy-10-octadecenoic acid and 11,12,13-trihydroxy-9(Z),15(Z)-octadecadienoic acid, isolated from rice plants with blast disease, exhibited antifungal activity, (T. Kato et al., "Structure and Synthesis of Unsaturated Trihydroxy C-18 Fatty Acids in Rice Plant Suffering from Rice Blast Disease", *Tetrahedron Lett.* 26:2357–2360, 1985), (H. Suemune et al., "Synthesis of Unsaturated Trihydroxy C-18 Fatty Acids Isolated from Rice Plants Suffering from Rice Blast Disease", *Chem. Pharm. Bull.* 36:3632–3637, 1988), (B. Gosse-Kobo et al., "Total Synthesis of Unsaturated Trihydroxy C-18 Fatty Acids", *Tetrahedron Lett.* 30:4235–4236, 1989) and (T. Kato et al., "Structure and Synthesis of 11,12,13-Trihydroxy-9(Z), 15(Z)-Octadecadienoic Acids from Rice Plant Suffering Rice Blast Disease", *Chem Lett.* 27:577–580, 1986). 9,12,13-Trihydroxy-10(E)-octadecenoic acid was also isolated from *Colocasia antiguorum* inoculated with *Ceratocystis fimbriata* and was shown to possess anti-black rot fungal activity, (H. Masui et al., "An Antifungal Compound, 9,12,13-Trihydroxy-(E)-10-Octadecenoic Acid, from *Colocasia antiguorum* Inoculated with *Ceratocystis fimbriata", Phytochemistry* 28:2613–2615, 1989). Recently, Hou, (C. T. Hou et al., "A Novel Compound, 12,13,17-Trihydroxy-9(Z)-Octadecenoic Acid, from Linoleic Acid by a New Microbial Isolate Clavibacter sp. ALA2", *J. Am. Oil Chem. Soc.* 73:1359–1362, 1996) reported the first production of a trihydroxy unsaturated fatty acid, 12,13,17-trihydroxy-9(Z)-octadecenoic acid (THOA), by microbial transformation of linoleic acid with Clavibacter sp. ALA2.

SUMMARY OF THE INVENTION

We have now discovered that *Pseudomonas aeruginosa* strain PR3 is one of several *P. aeruginosa* strains to produce a novel compound, 7,10,12-trihydroxy-8(E)-octadecenoic acid (TOD) from ricinoleic acid. TOD and its derivatives have activity in controlling biological organisms such as fungal diseases and insect pests. TOD is useful in field-control of certain diseases and pests on crops, and also in stored grains and other agricultural commodities.

In accordance with this discovery, it is an object of the invention to provide a novel chemical compound, TOD and derivatives thereof.

It is also an object of the invention to produce TOD from ricinoleic acid by bioconversion with *P. aeruginosa.*

It is a further object of the invention to provide a novel selective antifungal agent useful for controlling fungus growth and fungal metabolite production in field crops and in stored agricultural commodities.

Another object of the invention is to provide a selective insect control agent.

Other objects and advantages of the invention will be readily apparent from the ensuing description.

DEPOSIT OF BIOLOGICAL MATERIAL

*Pseudomonas aeroginosa* strain PR3 was deposited under the terms of the Budapest Treaty in the USDA, Agricultural Research Service Patent Culture Collection in Peoria, Ill., on Jan. 30, 1990, and has been assigned Accession No. NRRL B-18602. All restrictions on the availability of this deposit have been removed.

DETAILED DESCRIPTION OF THE INVENTION

The chemical structure of the TOD family of compounds within the scope of the invention is as follows:

FORMULA I

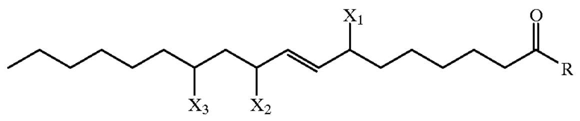

wherein:

R is—$(O)_n$—$R_1$, n is 0,1, and $R_1$ is H, or a hydrocarbon selected from the group consisting of substituted or unsubstituted alkyl, phenyl, or alkyl phenyl hydrocarbons, wherein the alkyl moiety may be branched or straight chain; and wherein:

$X_1$, $X_2$, and $X_3$ are independently selected from hydroxyl, halogen, or $NR_2R_3$, wherein $R_2$ and $R_3$ are independently selected from the group consisting of hydrogen, substituted or unsubstituted alkyl, phenyl, or alkyl phenyl hydrocarbons, wherein the alkyl moiety may be branched or straight chain.

Of particular interest is the compound TOD and lower, straight chain alkyl esters (1–6 carbons). In the ensuing discussion, it is understood that reference to TOD is intended to include TOD and the derivatives thereof encompassed by Formula I.

TOD is produced by cultivating *P. aeroginosa* strains, such as PR3 (Accession No. NRRL B-18602) on a suitable medium, such as a dextrose-containing medium, containing ricinoleic acid. A Wallen fermentation medium such as that disclosed in Example 1 is effective for producing TOD. The pH should be held in the range of about 6.5–8.0, and preferably about 7.3. The ricinoleic acid is added to established cultures (at least about 18 hours) in an amount ranging from about 0.25–5%, and preferably 0.5–1%. The fermentation is allowed to proceed aerobically for about 36–60 hours, preferably around 48 hours. Insofar as the *P. aeroginosa* may tend to utilize the TOD in the culture, the fermentation should be monitored and terminated when the TOD levels begin to decline.

The TOD may be isolated by a variety of means, including solvent extraction, liquid chromatography, high performance liquid chromatography, or the like. A methanol/ethyl acetate (1:9 v/v) is a suitable solvent system for TOD, though the skilled artisan would recognize that other solvent systems would also be operable. The degree of purification would depend upon the prospective end use of the compound, though for most uses it would be desired to isolate the compound in substantially pure form wherein the TOD is the major metabolite. Derivatives of TOD as encompassed within the scope of the above structural formula are obtainable by conventional reactions of hydroxy and/or carbonyl functional groups as known in the art.

In practice, the TOD is formulated in an effective amount with a suitable carrier or vehicle and is applied to the desired target site of control against a biological organism. It is generally expected that actual amounts of TOD in the formulation will be on the order of parts per million. The target site could include the locus of the organism, such as on the surface of a plant subject to disease or insect attack. It could also include direct application to the pest itself. The TOD could be formulated and applied as a liquid spray, dust, or wettable powder. Formulations designed for these modes of application will usually include a suitable liquid or solid carrier together with adjuvants, such as wetting, sticking agents and the like to promote ease of application and maximum expression of biocontrol. Polysaccharides such as starch and cellulose, etc. and derivatives thereof are contemplated for inclusion in these formulations as carriers and sticking agents.

The expression "an effective amount" is used herein in reference to that quantity of TOD that is necessary to reduction in the level of activity of the biological organism relative to that occurring in an untreated control under suitable conditions of treatment as described herein. For instance, when the organism is a fungus, the control would be inhibition of the growth of the fungus. In the case where the organism is an insect pest, the control could be an antifeedant effect or a lethal effect. Another measure of effectiveness may be in terms of the reduction of the adverse effect (or damage) caused by the target organism to be controlled.

As previously indicated, one suitable use for TOD would be in the control of fungal attack on crop plants and seed heads in the field. TOD has proven to be effective in controlling a variety of pathogenic fungi classified in several taxa. Without limitation thereto, fungi susceptible to TOD include species responsible for plant diseases in peach blossom blight (pathogen not identified), potato late blight (*Phytophthora infestans*), rice blast (*Phyricularia grisea*), and rice sheath blight (*Rhizoctonia solani*). It could also be used to control fungal damage of harvested seed crops in storage, such as cereals, legumes, nuts and other commodities. It is further envisioned that TOD would find application as a seed coating to protect planted seed from fungal attack prior to germination. Actual effective amounts would vary depending on factors such as the target fungus, mode of application and environmental conditions at the time of treatment.

Another suitable use for TOD would be in the control of insects on crop plants or in stored agricultural commodities. As demonstrated in the Examples, below, TOD exhibits selective insecticidal activity against insects in various taxonomic genera. Without limitation thereto, TOD exhibits an insecticidal effect toward corn plant hopper, green peach aphid, two-spotted spider mite, and *Drosophila melanogaster* when applied to the locus of unhatched eggs and/or larvae at concentrations in the range of 200–250 ppm.

EXAMPLE 1

Production and Isolation of TOD Microorganisms.

Pseudomonas sp. PR3 was isolated from a water run-off of a pig farm located in Morton, Ill. The culture used in this study was previously maintained on TGY agar medium (Difco® Laboratories). It was subsequently transferred monthly for 6 months onto fresh TGY and screening agar media. The screening medium (SM) contained (per liter) 4 g dextrose, 0.5 g yeast extract, 10 g $(NH_4)_2HPO_4$, 2 g $K_2HPO_4$, 0.5 g $MgSO_4.7H_2O$, 0.014 g $ZnSO_4.7H_2O$, 0.01 g $FeSO_4.7H_2O$, 0.008 g $MnSO_4.H_2O$, and 0.1 g nicotinic acid, (C. T. Hou et al., "Production of a New Compound, 7,10-Dihydroxy-8(E)-Octadecenoic Acid from Oleic Acid by Pseudomonas sp. PR3", *J. Indust. Microbiol.* 7:123–130, 1991). The medium was adjusted to pH 7.0 with diluted phosphoric acid.

Chemicals

Oleic acid and ricinoleic acid (both of 99+% purity) were purchased from Nu Chek Prep, Inc. (Elysian, Minn.). All other chemicals were reagent-grade and used without further purification. Thin-layer precoated Silica Gel 60 plates were obtained from EM Separations Technology (Gibbstown, N.J.).

Bioconversion Reactions.

Bioconversions were carried out in either SM or modified Wallen fermentation (WF) medium. The WF medium contained (per liter) 4 g dextrose, 5 g yeast extract, 4 g $K_2HPO_4$, 0.5 g $MgSO_4.7H_2O$, and 0.0075 g $FeSO_4.7H_2O$, and its pH was adjusted to 7.3 with 3N $H_2SO_4$. Ricinoleic acid (0.5–1%) was added to an 18-h-old culture in 30 mL WF medium, and the bioconversion was allowed to proceed for 2–3 days at 28° C. and 200 rpm. At the end of the conversion, lipids were recovered from the acidified broth by extracting twice with an equal volume of methanol/ethyl acetate (1:9; v/v). The solvent was then removed from the combined extracts with a rotary evaporator. The concentrated lipid extracts were transferred to one-dram vials and dried under a nitrogen stream for further analysis.

Analysis of Products

Bioconversion was monitored by gas chromatography (GC), thin-layer chromatography (TLC), and mass spectrometry (MS). Lipid extracts were esterified with diazomethane. The methyl esters were injected into an HP (Hewlett Packard; Palo Alto, Calif.) model 5890 Series II gas chromatograph, equipped with a Supelco (Bellefonte, Pa.) SPB-1 capillary column (15 m×0.32 mm, 0.25 μm film thickness), a flame ionization detector and an HP 7673 autosampler, and HP ChemStation software was used for data acquisition and integration. The temperature of the injector and the detector was set at 240° C. and 250° C., respectively, and helium was used as carrier gas at 1 mL/min. The oven temperature was programmed as follows: 190 to 204° C. at 2° C. per min, 204 to 230° C. at 5° C. per min, and holding at 230° C. for an additional 12 min. The quantitation of TOD was determined by total recovery weights.

TLC analyses were carried out on Silica Gel 60 (0.25 mm thickness) plates (EM Science, Gibbstown, N.J.), developed in chloroform/methanol/acetic acid (9:1:0.1, by vol.). The chromatograms were visualized first with sulfuric acid spray, followed by charring with a heat gun, and then with vanillin/sulfuric acid spray, followed by brief heating.

Isolation and Identification of TOD

The products were separated in a mini-column (7 cm×5 mm i.d.) of Silica Gel 60 (230–400 mesh) with a gradient of hexane and ethyl acetate. The column was washed with two bed volumes of hexane/ethyl acetate (20:80; v/v). A portion of the products (55 mg) in a minimal volume of the column wash solvent was then applied onto the column. Subsequent column elution was carried out by the following sequential steps: Four bed-volumes wash solvent, one bed-volume 100% ethyl acetate, two bed-volumes 100% ethyl acetate, and one bed-volume ethyl acetate/methanol (50:50; v/v) to yield a homogeneous fraction as indicated by TLC. The isolated material was further analyzed by GC-mass spectrometry (GC-MS) and nuclear magnetic resonance (NMR).

The sample was first methylated, and trimethylsilyl (TMS) derivatives were subsequently prepared by using Sylon BTZ (Supelco, Bellefonte, Pa.) according to the manufacturer. Electron-impact GC-MS was obtained with an HP model 5890 gas chromatograph, coupled to an HP model 5972 mass selective detector. Separations of components were achieved in an HP-5 (30 m×0.25 mm i.d., 0.25 μm film thickness) column with a temperature gradient programmed to start at 70° C., increasing at 20° C./min to 170° C. with 1 min hold at this temperature, increasing at 5° C./min to 250° C. and holding for 15 min. The underivatized sample was analyzed by proton and $^{13}C$-NMR as described by Hou et al., (C. T. Hou et al., "Production of a New Compound, 7,10-Dihydroxy-8(E)-Octadecenoic Acid from Oleic Acid by Pseudomonas sp. PR3", *J. Indust. Microbiol.* 7:123–130, 1991).

Strain PR3 converted ricinoleic acid to produce TOD. This novel compound has a characteristic retention time (RT) of 14.17 min, whereas DOD had an RT of 10.89 min and the internal standard, palmitic acid, had an RT of 2.86 min. Production of TOD appears to be sensitive to the time for conducting the fermentation. By extending the conversion time from 48 to 72 h prior to lipid extraction, the yield of new compound, relative to the GC peak area of methyl palmitate, decreased from 20.0% to 2.3%. This indicated that TOD formed in the culture medium could be further metabolized by strain PR3. The yield of this bioconversion reaction was 35.2%, based on the total weights of compound recovered from a TLC separation.

Structure Determination of TOD: NMR Analysis

Proton NMR showed the following resonance signals: olefinic protons —CH═CH— at 5.65 ppm; three tertiary protons —CH—O— at 4.30 ppm, 4.01 ppm, and 3.79 ppm, with the first two being adjacent to a double bond; $—CH_2—COOH$ at 2.27 ppm; methylene groups ranged from 1.30 to 1.62 ppm; and a terminal $—CH_3$ at 0.90 ppm. The coupling constant was 15 Hz for the olefinic products, indicating a possible trans-configuration across the double bond. The $^{13}C$-NMR spectra showed three carbon peaks at 69.03, 69.78, and 73.00 ppm, characteristic of a hydroxyl attachment. There was a distinct methylene carbon at 45.69 ppm and two olefinic carbons at 133.87 and 135.02 ppm. The remaining carbon peaks were at 14.44, 23.70, 26.11, 26.28, 26.71, 30.17, 30.50, 33.05, 35.02, 38.23, 38.96, and 177.80 ppm. The NMR data indicate that this compound is a trihydroxy octadecenoic acid with a trans-configuration and that a methylene group interrupts two of the three carbons each bearing a hydroxyl group.

GC-MS Analysis

The electron impact mass spectrum of TMS derivatives of the methylated sample showed that seven m/z peaks with their corresponding relative intensities were important to the structure determination: 187(100%), 231(19%), 359(11%), 431(1.8%), 239(46%), 269(11%), and 341(5%). As shown in FIG. 1, m/z 187 was the fragment from the terminal methyl end of the molecule with a hydroxyl group at the C-12 position. The fragment from the carboxyl end with a second hydroxyl group attached to the C-7 position corresponded to ion m/z 231. The assignment of a hydroxyl group at the C-7 position was consistent with the presence of a large fragment at m/z 431. The release of a trimethylsilyl group from m/z 431 produced fragment ion m/z 341. The third hydroxyl group was present at the C-10 position as shown in a fragment of m/z 359. Releasing of TMS from C-10 produced the ion of m/z 269. Fragment ion m/z 329 had been converted to m/z 239 upon the release of TMS due to rearrangement of the double bond at the C-8 position. These fragments located the hydroxyl groups at C-7, C-10, and C-12 and the double bond at C-8 of the molecule. Based on both NMR and MS data, it was concluded that the new compound as produced by transformation of ricinoleic acid with strain PR3 is 7,10,12-trihydroxy-8(E)-octadecenoic acid (TOD).

EXAMPLE 2

Testing of Anti-Plant Pathogenic Fungal Activity

A concentration of 5 parts per million (ppm) of TOD was formulated in a mixture of 50:50 acetone:water solvent. The TOD solution (15 mL) was used to spray each test plant with an air-assisted nozzle. Included in the tests were replicated standards, two for each pathogen. After 24 h, the plant was inoculated with the pathogenic fungus. Obligate pathogens were grown on the host plant. Spores were collected, put into a titered solution based on the pathogen and sprayed on the test plants. All other pathogens were grown in vitro on agar (pathogen dependent), harvested, titered and sprayed onto the test plants. Test plants were then incubated for a period of 24 to 48 h (pathogen dependent) after which it was placed in a growth chamber. Plants were rated 4 to 5 days after inoculation. The data were reported as percent disease control.

The biological activity of TOD was tested agaist pathogenic fungi that caused plant diseases in peach blossom blight (pathogen not identified), potato late blight (*Phytophthora infestans*), rice blast (*Phyricularia grisea*), rice sheath blight (*Rhizoctonia solani*), wheat foot rot (*Pseudocercosporella hexpotrichoides*), and wheat glume blotch (*Septoria nodorum*). At 5 ppm concentration, TOD exhibited 29% disease control against rice blast, 21% control against rice sheath blight, 20% control against peach blossom blight, 1% control against potato late blight and no controls against diseases of wheat foot rot and wheat glume blotch.

EXAMPLE 3

Testing of Insecticide Activity

TOD was formulated in a 75:25 mixture of acetone:water solvent. The formulated solution was applied at a desired concentration by a hydraulic belt sprayer. In each test, replicated controls of untreated and solvent alone, as well as insecticide standards were included as references. The standards selected were contemporary products commonly used for insect control in production agriculture. Eight days after spraying, the test units were read for the number of unhatched eggs or dead larvae. The insecticide activity of the test compound was expressed as the percentage of what resulted from the action by the insecticide standards, 0% being no insect control and 100% being complete control. A reading of less than 100% placed the test compound in the category of weak insecticide activity.

TOD was tested against insects, corn planthopper, *Culex pippiens, Drosophila melanogaster*, fall army worm, green peach aphid, southern corn rootworm, and two-spotted spider mite. TOD showed no insecticide activity toward *Culex pippiens*, fall army worm, and southern corn rootworm. The results also indicated that TOD exhibited low activity against corn plant hopper (80%), green peach aphid (80%), and two-spotted spider mite (90%) at 250 ppm concentration, and good activity toward *Drosophila melanogaster* (100%) at 200 ppm concentration.

We claim:

1. A method of controlling a biological organism comprising applying to the locus of said organism an effective amount of a compound having the formula:

FORMULA I

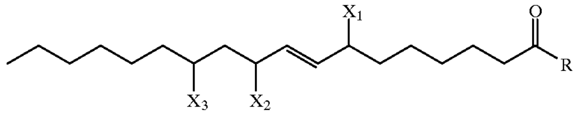

wherein:

R is $-(O)_n-R_1$, n is 0,1, and $R_1$ is H, or a hydrocarbon selected from the group consisting of substituted or unsubstituted alkyl, phenyl, or alkyl phenyl hydrocarbons, wherein the alkyl moiety may be branched or straight chain; and wherein:

$X_1$, $X_2$, and $X_3$ are independently selected from hydroxyl, halogen, or $NR_2R_3$, wherein $R_2$ and $R_3$ are independently selected from the group consisting of hydrogen, substituted or unsubstituted alkyl, phenyl, or alkyl phenyl hydrocarbons, wherein the alkyl moiety may be branched or straight chain.

2. The method of claim 1 wherein said compound is applied to a substrate.

3. The method of claim 2 wherein said substrate is a plant.

4. The method of claim 3 wherein said plant is a cereal crop plant.

5. The method of claim 2 wherein said substrate is the seed of a plant.

6. The method of claim 2 wherein said substrate is harvested seed.

7. The method of claim 6 wherein said harvested seed is selected from the group consisting of cereals, legumes, and nuts.

8. The method of claim 1 wherein said biological organism is a fungus or an insect.

9. The method of claim 1 wherein $X_1$, $X_2$, and $X_3$ are all hydrogen.

10. The method of claim 1, wherein $X_1$, $X_2$, and $X_3$ are all hydrogen and R is hydrogen or a C1 to C6 straight chain alkyl group.

11. The method of claim 1 wherein said compound is 7,10,12-trihydroxy-8(E)-octadecenoic acid.

12. A formulation comprising:

1) a compound having the formula:

FORMULA I

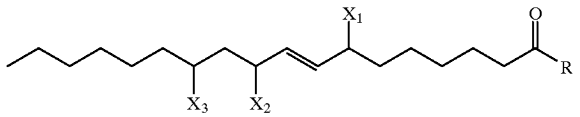

wherein:

R is $-(O)_n-R_1$, n is 0,1, and $R_1$ is H, or a hydrocarbon selected from the group consisting of substituted or unsubstituted alkyl, phenyl, or alkyl phenyl hydrocarbons, wherein the alkyl moiety may be branched or straight chain; and wherein:

$X_1$, $X_2$, and $X_3$ are independently selected from hydroxyl, halogen, or $NR_2R_3$, wherein $R_2$ and $R_3$ are independently selected from the group consisting of hydrogen, substituted or unsubstituted alkyl, phenyl, or alkyl phenyl hydrocarbons, wherein the alkyl moiety may be branched or straight chain; and 2) a carrier for said compound;

wherein said compound is present in an effective amount for controlling a biological organism.

13. The formulation of claim 12, wherein $X_1$, $X_2$, and $X_3$ are all hydrogen.

14. The formulation of claim 12, wherein $X_1$, $X_2$, and $X_3$ are all hydrogen and R is hydrogen or a C1 to C6 straight chain alkyl group.

15. The formulation of claim 12, wherein said compound is 7,10,12-trihydroxy-8(E)-octadecenoic acid.

16. The compound having the formula:

FORMULA I

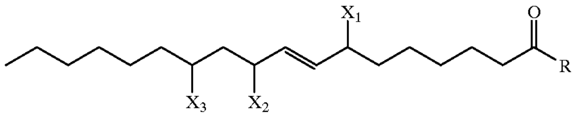

wherein:

R is —(O)$_n$—$R_1$, n is 0,1, and $R_1$ is H, or a hydrocarbon selected from the group consisting of substituted or unsubstituted alkyl, phenyl, or alkyl phenyl hydrocarbons, wherein the alkyl moiety may be branched or straight chain; and wherein:

$X_1$, $X_2$, and $X_3$ are independently selected from hydroxyl, halogen, or $NR_2R_3$, wherein $R_2$ and $R_3$ are independently selected from the group consisting of hydrogen, substituted or unsubstituted alkyl, phenyl, or alkyl phenyl hydrocarbons, wherein the alkyl moiety may be branched or straight chain.

17. The compound of claim 1, wherein $X_1$, $X_2$, and $X_3$ are all hydrogen.

18. The compound of claim 1, wherein $X_1$, $X_2$, and $X_3$ are all hydrogen and R is hydrogen or a C1 to C6 straight chain alkyl group.

19. The compound of claim 1 wherein said compound is 7,10,12-trihydroxy-8(E)-octadecenoic acid.

* * * * *